(12) United States Patent
Zhang et al.

(10) Patent No.: US 10,408,718 B2
(45) Date of Patent: Sep. 10, 2019

(54) THREE-DIMENSIONAL NON-UNIFORM LOADING/UNLOADING AND STEADY PRESSURE MODEL TEST SYSTEM

(71) Applicant: SHANDONG UNIVERSITY, Jinan (CN)

(72) Inventors: Qiangyong Zhang, Jinan (CN); Chuancheng Liu, Jinan (CN); Shucai Li, Jinan (CN); Wen Xiang, Jinan (CN); Hanpeng Wang, Jinan (CN); Yue Zhang, Jinan (CN); Mingyang Ren, Jinan (CN); Dong Wu, Shijiazhung (CN)

(73) Assignee: SHANDONG UNIVERSITY, Jinan (CN)

( * ) Notice: Subject to any disclaimer, the term of this patent is extended or adjusted under 35 U.S.C. 154(b) by 0 days.

(21) Appl. No.: 15/762,712

(22) PCT Filed: Apr. 28, 2017

(86) PCT No.: PCT/CN2017/082448
§ 371 (c)(1),
(2) Date: Mar. 23, 2018

(87) PCT Pub. No.: WO2018/195919
PCT Pub. Date: Nov. 1, 2018

(65) Prior Publication Data
US 2019/0078987 A1     Mar. 14, 2019

(51) Int. Cl.
*G01N 3/06*     (2006.01)
*G01N 33/24*    (2006.01)
*G01N 3/12*     (2006.01)

(52) U.S. Cl.
CPC ............... *G01N 3/064* (2013.01); *G01N 3/12* (2013.01); *G01N 33/24* (2013.01);
(Continued)

(58) Field of Classification Search
CPC .. G01N 3/064; G01N 3/12; G01N 2203/0019; G01N 2203/0256;
(Continued)

(56) References Cited

U.S. PATENT DOCUMENTS

| 9,188,520 B1 * | 11/2015 | Smith ...................... G01N 3/08 |
| 2015/0020603 A1 * | 1/2015 | Kismarton .......... G01M 5/0091 73/800 |

FOREIGN PATENT DOCUMENTS

| CN | 1793828 A | 6/2006 |
| CN | 101285808 A | 10/2008 |

(Continued)

OTHER PUBLICATIONS

Jan. 25, 2018 International Search Report issued in Patent Application No. PCT/CN2017/082448.
(Continued)

*Primary Examiner* — Daniel S Larkin
*Assistant Examiner* — Anthony W Megna Fuentes
(74) *Attorney, Agent, or Firm* — Oliff PLC

(57) ABSTRACT

A pressure three-dimensional non-uniform loading/unloading and steady pressure model test system has a pressure three-dimensional non-uniform loading/unloading device. The pressure three-dimensional non-uniform loading/unloading device is controlled via an input instruction of the hydraulic loading/unloading and steady pressure automatic control system to carry out pressure three-dimensional gradient non-uniform loading/unloading and steady pressure control. An automatic model displacement test system automatically acquires the displacement of any part inside a test model. A multi-probe peeping system observes a cavern excavation deformation and failure process dynamically in real time.

16 Claims, 13 Drawing Sheets

(52) U.S. Cl.
CPC ........... *G01N 2203/0003* (2013.01); *G01N 2203/0019* (2013.01); *G01N 2203/0048* (2013.01); *G01N 2203/0208* (2013.01); *G01N 2203/0256* (2013.01); *G01N 2203/0641* (2013.01); *G01N 2203/0682* (2013.01)

(58) Field of Classification Search
CPC ... G01N 2203/0208; G01N 2203/0682; G01N 2203/0003; G01N 2203/0048; G01N 3/08; G01N 3/02; G01N 3/00; G01N 33/00; G01N 2203/0016; G01N 2203/0085; G01M 99/007; G01M 5/0075
See application file for complete search history.

(56) References Cited

FOREIGN PATENT DOCUMENTS

| | | |
|---|---|---|
| CN | 101344444 A | 1/2009 |
| CN | 201247116 Y | 5/2009 |
| CN | 102175517 A | 2/2011 |
| CN | 102879550 A | 1/2013 |
| JP | 2003-050188 A | 2/2003 |

OTHER PUBLICATIONS

Article from the Journal of Hydraulic Engineering, vol. 12, (2002).
Kedu, Liang et al., "Experimental Analysis on Stability and Support in Surrounding Rocks of Underground Power Houses.", Journal of Wuhan Univeristy of Hydraulic and Electrical Engineering, vol. 25, No. 5, pp. 461-469, (1992).
Qiangyong, Zhang et al., "A geotechnical-geomechanics model test system and its application.", China Civil Engineering Journal, vol. 39, No. 12, pp. 100-104, (2006).
Anmin, Chen et al., "Development and Application of Multifunctional Apparatus for Geotechnical Engineering Model Tests.", Chinese Journal of Rock Mechanics and Engineering, vol. 3, pp. 372-378, (2004).
Jongpradist, Pornkasem et al., "High internal pressure induced fracture patterns in rock masses surrounding caverns: Experimental study using physical model tests.", Engineering Geology, vol. 197, pp. 158-171, (2015).
Yang, Xuxu et al., "Numerical simulation of a jointed rock block mechanical behavior adjacent to an underground excavation and comparison with physical model tests results.", Tunnelling and Underground Space Technology, vol. 50, pp. 129-142, (2015).
Weishen, Zhu et al., "Quasi-three-dimensional physical model tests on a cavern complex under high in-situ stresses.", International Journal of Rock Mechanics and Mining Sciences, vol. 48, pp. 199-209, (2011).
He, Mancho, "Physical modeling of an underground roadway excavation in geologically 45 degree inclined rock using infrared thermography.", Engineering Geology, vol. 121, pp. 165-176, (2011).
Shin, Jong-Ho et al., "Model testing for pipe-reinforced tunnel heading in a granular soil.", Science Direct, Tunnelling and Underground Space Technlogy, vol. 23, pp. 241-250, (2008).
Castro, R. et al., "A study of isolated draw zones in block caving mines by means of a large 3D physical model.", Science Direct, International Journal of Rock Mechanics and Mining Sciences, vol. 44, pp. 860-870, (2007).

* cited by examiner

Note: solid arrows indicate instructions, and hollow arrows indicate detection signals

THREE-DIMENSIONAL NON-UNIFORM LOADING/UNLOADING AND STEADY PRESSURE MODEL TEST SYSTEM

FIELD OF THE INVENTION

The present invention relates to an intelligent numerically-controlled ultrahigh pressure true three-dimensional non-uniform loading/unloading and steady pressure model test system used in the field of deep underground engineering, such as hydropower, traffic, energy, mines, national defense engineering and so on.

BACKGROUND OF THE INVENTION

With the rapid development of the global economy, the shallow mineral resources of the earth are gradually depleted, and the development of resources continually goes deep into the earth. At the same time, the demands of human survival and development and the exploration on the unknown world are also constantly expanding the underground activity space. At present, many underground works that are being built and to be built in China continue to enter the deep part, for example, traffic tunnels, mine roadways, hydropower caverns, oil and gas storage caverns and the like are gradually developed to one or several kilometers. With the increase of excavation depths of underground works, the geological occurrence environment of deep cavern surrounding rock is increasingly complex. Under the "three-high and one-disturbance" condition of high geostress, high seepage pressure, high earth temperature and excavation disturbance, nonlinear deformation and failure phenomena significantly different from those in shallow buried caverns appear in deep caverns, e.g., large deformation, zonal disintegration, rock burst, water outburst and mud outburst, coal and gas outburst and other disasters often cause heavy casualties and economic loss and bad social impact. The traditional theories, methods and technologies of shallow rock mass have been unable to solve the nonlinear failure problem of deep rock mass. It is urgent to further study the nonlinear deformation characteristics and failure mechanism of the deep cavern surrounding rock. However, in the face of the complex nonlinear deformation and failure phenomena of the deep caverns, the traditional theories and methods are hardly competent, the numerical simulation is difficult, the in-situ test condition is limited and cost is very expensive, and by contrast, the geomechanical model test, which is vivid, intuitive and real, has become an important means of studying the nonlinear deformation and failure rules of the deep cavern. Different from MTS which can only study the mechanical characteristics of small-sized rock core specimens, the geomechanical model test is a physical simulation method for studying the engineering construction and deformation-failure process by using a reduced scale geological model according to the similarity principle. The geomechanical model test can provide supplementation and validation for the numerical simulation, can subtly simulate the nonlinear deformation and failure process of underground cavern excavation and the global degree of safety of a cavern group system, and plays an irreplaceable important role in discovering new phenomena, revealing new mechanisms, exploring new rules and validating new theories. In order to carry out the model test of underground engineering, it is necessary to have a geomechanics model test system. At present, the research status of the related geomechanical model test system is as follows:

(1) International Journal of Rock Mechanics and Mining Sciences, Issue 44, 2007, introduced a three-dimensional model test system for simulating mining, which cannot implement true three-dimensional non-uniform loading/unloading.

(2) Tunnelling and Underground Space Technology, Issue 23, 2008, introduced a geomechanical model test system for simulating sandy soil pipe roof construction, and this system can only implement geostatic stress loading, but cannot realize true three-dimensional non-uniform loading/unloading.

(3) International Journal of Engineering Geology, Issue 121, 2011, introduced a PFESA (Physically Finite Elemental Slab Assemblage) model test system, and this system can only implement uniform loading of plane stress, but cannot realize true three-dimensional non-uniform loading/unloading.

(4) International Journal of Rock Mechanics & Mining Sciences, Issue 48, 2011, introduced a quasi-three-dimensional geomechanical model test system, the single-sided maximum working pressure of the system is 300kN, and the system can simulate the state of plane stress, but cannot realize true three-dimensional non-uniform loading/unloading.

(5) Tunnelling and Underground Space Technology, Issue 50, 2015, introduced a plane stress test device, and the device can only implement vertical self-weight loading, but cannot realize true three-dimensional non-uniform loading/unloading.

(6) International Journal of Engineering Geology, Issue 197, 2015, introduced a model test system, the system applies air pressure via a built-in airbag in a model, the circumference of the model is passively constrained, and true three-dimensional non-uniform loading/unloading cannot be realized.

(7) Journal of Wuhan Hydraulic Power University, Issue 5, 1992, introduced a plane stress loading system, in which pressure is controlled by an air pump to be gradually loaded or unloaded, the system can only carry out plane loading, but cannot realize true three-dimensional non-uniform loading/unloading.

(8) Chinese Journal of Rock Mechanics and Engineering, Issue 3, 2004, introduced a multifunctional geotechnical engineering simulation test device, composed of upper and lower cover plates, a triangular distribution block and three sets of mutually perpendicular orthogonal pulling rod systems, and the device loads small-sized specimens and cannot realize high geostress non-uniform loading/unloading.

(9) Journal of Hydraulic Engineering, Issue 5, 2002, introduced a discrete multi principal stress surface loading test system, the loading system is mainly composed of a high-pressure airbag, a reverse thrust plate, a limiting jack and an air compressor, and the loading system cannot realize high geostress true three-dimensional non-uniform loading/unloading.

(10) China Civil Engineering Journal, Issue 12, 2005, introduced a rock-soil geomechanical model test system, mainly composed of a bench counterforce device, a variable load loading plate and a hydraulic loading control test bed, and the system can only load plane strain with a limited loading value, but cannot implement true three-dimensional loading/unloading of a deep cavern.

In general, the existing geomechanical model test systems at home and abroad have the following problems:

1) The loading counterforce device of the model test system is fixed in size, and cannot be randomly adjusted according to the range of the test model;

2) The model test system is mainly based on planar, quasi three-dimensional, small-sized and uniform loading, and cannot implement the true three-dimensional non-uniform loading/unloading process;

3) The model test system loads a small load, and cannot truly simulate the high stress distribution state of deep rock mass via ultrahigh pressure loading;

4) The model test system cannot automatically acquire the displacement of any part inside the model.

SUMMARY OF THE INVENTION

In order to overcome the above defects of the prior art, the present invention provides an intelligent numerically-controlled ultrahigh pressure true three-dimensional non-uniform loading/unloading and steady pressure model test system with the advantages of digital servo control, large loading value, high loading precision, good steady pressure performance, large and adjustable device size and capability of simulating an ultrahigh pressure non-uniform loading/unloading and steady pressure process and observing the deformation failure process of the deep cavern.

The objective of the present invention is realized by adopting the following technical solution:

An intelligent numerically-controlled ultrahigh pressure true three-dimensional non-uniform loading/unloading and steady pressure model test system, including a combined bench counterforce device, an ultrahigh pressure true three-dimensional non-uniform loading/unloading device, an intelligent hydraulic loading/unloading and steady pressure numerical control system, an automatic model displacement test system and a high-definition multi-probe peeping system, wherein the combined bench counterforce device is formed by connecting detachable box-type members, adjustable in size, used for accommodating a test model and used as a counterforce device for loading in test, the ultrahigh pressure true three-dimensional non-uniform loading/unloading device is arranged in the combined bench counterforce device and used for carrying out ultrahigh pressure true three-dimensional loading/unloading on the test model, and the intelligent hydraulic loading/unloading and steady pressure numerical control system is connected with the ultrahigh pressure true three-dimensional non-uniform loading/unloading device via a high-pressure oil pipe; the ultrahigh pressure true three-dimensional non-uniform loading/unloading device is controlled in a digital servo manner via an input instruction of the intelligent hydraulic loading/unloading and steady pressure numerical control system to carry out ultrahigh pressure true three-dimensional gradient non-uniform loading/unloading and steady pressure control; the automatic model displacement test system automatically acquires the displacement of any part inside the model; and the high-definition multi-probe peeping system observes a cavern excavation deformation and failure process dynamically in real time.

Further, the combined bench counterforce device formed by connecting detachable box-type members includes a box-type bottom beam, a box-type top beam, a box-type left upright post, a box-type right upright post, a box-type front counterforce wall member and a box-type rear counterforce wall member; the box-type bottom beam and the box-type top beam are distributed up and down and connected with each other via the box-type left and right upright posts to form a rectangular frame structure, the box-type front counterforce wall member and the box-type rear counterforce wall member are arranged in the front and the back of the rectangular frame, and the whole combined bench counterforce device is combined via a connecting device.

Further, a transparent excavation window is arranged in the middle of the box-type front counterforce wall and mainly composed of a high-strength steel frame and a toughened glass panel, and a cavern excavation window is arranged in the center of the toughened glass panel.

Further, the ultrahigh pressure true three-dimensional non-uniform loading/unloading device includes a plurality of loading units which are respectively fixed on the upper, lower, left, right and rear surfaces of the combined bench counterforce device to carry out active true three-dimensional loading, and the front of the model adopts a displacement constrained passive loading manner.

Further, 33 loading units are included and divided into eight groups, six loading units in the first group are arranged at the top of the model, six loading units in the second group are arranged at the bottom of the model, and six loading units are arranged on each of the left and right sides of the model and divided into three groups from top to bottom with each group including four loading units; and nine loading units are arranged on the rear surface of the model and divided into three groups from top to bottom with each group including three loading units.

Further, the eight groups of loading units respectively carry out independent and synchronous ultrahigh pressure gradient non-uniform loading/unloading via eight oil ways controlled by the intelligent hydraulic loading/unloading and steady pressure numerical control system.

Further, each loading unit includes a hydraulic jack and a bench-type force transfer loading module; the bottom of the bench-type force transfer loading module clings to a loading steel plate on the surface of the model, the top of the bench-type force transfer loading module is connected with the front end of the hydraulic jack by adopting a connecting device, and the rear end of the hydraulic jack is connected to the inner wall of the combined bench counterforce device via a connecting device; and the load of the hydraulic jack can be uniformly applied to the test model by using the bench-type force transfer loading module and the combined bench counterforce device.

Further, a loading guide frame device is arranged close to the exterior of the test model, and the guide frame device is formed by welding stainless steel square tubes; and before loading, the loading steel plate of the model clings to the surface of the test model and is embedded into the guide frame device a certain depth.

Further, the intelligent hydraulic loading/unloading and steady pressure numerical control system is mainly composed of a visual human-machine interaction system, a PLC hydraulic numerical control system and an ultrahigh pressure execution system; the visual human-machine interaction system transmits information with the PLC hydraulic numerical control system; and the PLC hydraulic numerical control system transmits information with the ultrahigh pressure execution system.

Further, the visual human-machine interaction system includes a human-machine interface (HMI), a PC monitoring system and a software system; the PLC hydraulic numerical control system includes a central control unit, a pressure output unit and a pressure detection unit; the ultrahigh pressure execution system includes a hydraulic oil way system and hydraulic jacks; the software system is installed on the HMI and the PC monitoring system, and the PC monitoring system transmits information with the central control unit and the HMI; the HMI also transmits information with the central control unit, the central control unit controls the pressure output unit, the pressure output unit controls the hydraulic oil way system, and the hydraulic oil way system controls hydraulic jacks; the pressure detection unit detects pressure information of hydraulic jacks and feeds the pressure information back to the central control unit, the central control unit synchronously transmits the detected pressure information to the HMI or the PC monitoring system, and the pressure information is displayed on the HMI or the PC monitoring system.

The hydraulic oil way system includes step motors, oil pumps, step overflow valves, O-shaped three-position four-way electromagnetic reversing valves, electromagnetic ball valve pressure retaining valves and synchronous valves; the step overflow valve is used for adjusting the pressure of an oil way, the O-shaped three-position four-way electromagnetic reversing valve is used for controlling the flow direction of the oil way, the electromagnetic ball valve pressure retaining valve is used for retaining the pressure, and the synchronous valve is used for synchronous loading. The step motor starts the oil pump to pump hydraulic oil into the oil way, the hydraulic oil enters the step overflow valve, and the PLC hydraulic numerical control system controls the step motor according to the pressure feedback information detected by the pressure detection unit in real time to adjust the valve core of the step overflow valve to advance or retreat to reduce or increase the pressure of the oil way, thus completing a loading/unloading process; and when the pressure of the hydraulic oil way system is changed, the PLC hydraulic numerical control system controls the step overflow valve in a servo manner to increase or reduce the pressure to realize instantaneous pressure supplement, and the electromagnetic ball valve pressure retaining valve keeps the loading system in a steady pressure state. In addition, the starting pressure of the hydraulic oil way system can be reduced to 0 MPa via variable frequency debugging of the step overflow valve in combination with the stepless speed adjustment of the step motor to realize zero pressure start.

Specifically, when the model is loaded/unloaded, an operator inputs a loading/unloading value via the HMI or the PC monitoring system of the visual human-machine interaction system, and the visual human-machine interaction system transmits a loading/unloading instruction to the PLC hydraulic numerical control system; the PLC hydraulic numerical control system converts the digital pressure signal into an electrical signal and transmits the electrical signal to the ultrahigh pressure execution system, and the ultrahigh pressure execution system receives the electrical signal and controls the step motor to adjust the valve core of the step overflow valve to advance or retreat to reduce or increase the pressure of the oil way, thus completing the loading/unloading process. The loading pressure can be reduced to 0 MPa via variable frequency debugging of a step overflow valve drive system to realize zero pressure start. The pressure detection unit detects the pressure change of hydraulic jacks dynamically in real time and feeds pressure change information back to the central control unit of the PLC hydraulic numerical control system in time, the central control unit synchronously transmits the processed digital pressure information to the HMI or the PC monitoring system, and the digital pressure information is displayed on the HMI or the PC monitoring system. The pressure change history of the oil way is automatically stored by the human-machine interaction system.

Further, the automatic model displacement test system is mainly composed of a displacement transfer device, a displacement measuring device, a signal conversion device, a data processing device and a computer system; the displacement transfer device detects the displacement of the test model, the displacement measuring device transmits the displacement information to the signal conversion device, the signal conversion device transmits information with the data processing device, and the data processing device transmits information with the computer.

Further, when the model produces a displacement, the displacement transfer device transfers the displacement of a model measuring point to the displacement measuring device via a flexible measuring rod, and the displacement measuring device converts the displacement of the model measuring point into a moire fringe displacement via a grating ruler sensor thereof; the signal conversion device converts the moire fringe displacement into an electric pulse signal via a photoelectric conversion element thereof and transmits the electric pulse signal to the data processing device; the data processing device receives the electric pulse signal and converts the electric pulse signal into a digital signal, then the displacement of the model is calculated out and stored and displayed on the computer interface in real time, meanwhile, a model displacement time-history curve is automatically generated for a tester to dynamically observe and monitor the displacement of the model, so that digital, visual and intelligent automatic measurement of the displacement of the model is realized.

Further, the high-definition multi-probe peeping system is mainly composed of a plurality of micro high-definition probes, a high-speed camera control panel, a data storage box and a liquid crystal display; the plurality of micro high-definition probes are arranged at any inner or outer part of a model cavern; and the acquired video is displayed on the liquid crystal display in real time and automatically stored in a data storage.

Compared with the same model test systems at home and abroad, the present invention has the following significant advantages:

(1) The loading value of the present invention is large (the rated output of the system is 63 MPa, and the maximum load is 45000 kN), ultrahigh pressure true three-dimensional non-uniform loading/unloading and steady pressure control can be implemented, the non-uniform distribution status of high geostress of the deep rock mass buried more than kilometers as well as the nonlinear deformation failure process of the deep cavern excavation can be finely simulated, and the technical problems of low-pressure and uniform loading of the existing geomechanical model test system are solved.

(2) The loading precision of the present invention is high (1.50‰ F.S.), and the steady pressure time is long (over 300 days). Zero pressure start is realized via variable frequency debugging of the step overflow valve drive system; any loading/unloading cyclic model test can be performed via the intelligent hydraulic loading/unloading and steady pressure numerical control system, and the technical problems that the existing geomechanical model test system is low in loading precision and short in steady pressure time, cannot realize zero pressure start and cannot implement loading/unloading cyclic test are solved.

(3) The present invention is broad in loading range and high in degree of loading/unloading automation, can realize random loading/unloading of less than 63 MPa, can simulate the cavern failure under the ultra-deep high geostress environment, and can also simulate cavern failure under the shallow low geostress environment.

(4) The bench counterforce device of the present invention adopts a modular combined structure, so the test device is large in scale and adjustable in size, the size of the counterforce device can be randomly adjusted according to the model test range to meet the test requirements of different scale model test, and the technical problem that the size of the counterforce device of the existing geomechanical model system is fixed and non-adjustable is solved.

(5) The model displacement test of the present invention can automatically test the displacement of any part inside the model via the flexible transfer technology and the photoelectric conversion technology, the displacement measuring precision reaches 0.001 mm, and the present invention has stable test performance, is not disturbed by external electromagnetic fields, and solves the technical problem that the existing geomechanical model test cannot effectively test the displacement of any part inside the model.

(6) The present invention is equipped with the detachable transparent excavation window variable in shape and size and the high-definition multi-probe peeping system, so that the deformation and failure process of cavern excavation can be observed dynamically in real time.

BRIEF DESCRIPTION OF THE DRAWINGS

The accompanying drawings constituting a part of the present application are used for further understanding of the present application, and the schematic embodiments of the present application and the description thereof are used for interpreting the present application, rather than constituting improper limitation to the present application.

In which: 1—combined bench counterforce device, 2—ultrahigh pressure true three-dimensional non-uniform loading/unloading device, 3—intelligent hydraulic loading/unloading and steady pressure numerical control system, 4—automatic model displacement test system, 5—high-definition multi-probe peeping system, 6—box-type top beam, 7—box-type bottom beam, 8—box-type left and right upright posts, 9—box-type front counterforce wall, 10—box-type rear counterforce wall, 11—hydraulic jack, 12—ultrahigh pressure force transfer loading module, 13—three-dimensional loading guide frame device, 14—model loading steel plate, 15—high-pressure oil pipe, 16—high-strength bolt, 17—steel corner fitting, 18—test model, 19—model cavern, 20—tie bar, 21—jack flange plate, 22—force transfer loading module top plate, 23—force transfer loading module bottom plate, 24—force transfer reinforcing rib plates, 25—cavern excavation window, 26—division plate, 27—steel frame, 28—toughened glass panel, 29—PC monitoring system, 30—PLC hydraulic numerical control system, 31—ultrahigh pressure execution system, 32—network cable, 33—cable, 34—oil tank, 35—oil filter, 36—step motor, 37—oil pump, 38—step overflow valve, 39—pressure sensor, 40—O-shaped three-position four-way electromagnetic reversing valve, 41—electromagnetic ball valve pressure retaining valve, 42—synchronous valve, 43—collecting valve, 44—programmable controller, 45—human-machine interface HMI, 46—sensor system, 47—variable frequency oil pump drive system, 48—step overflow valve drive system, 49—electromagnetic valve drive system, 50—displacement measuring point, 51—PVC sleeve, 52—flexible thin wire rope, 53—anti-friction positioning disc, 54—grating ruler sensor, 55—displacement transfer pulley, 56—self-balancing hammer, 57—displacement test reference frame, 58—collapse failure mode of cavern.

DETAILED DESCRIPTION OF THE EMBODIMENTS

It should be pointed out that the following detailed description is exemplary and intends to further illustrate the present application. Unless otherwise specified, all technical and scientific terms used herein have the same meanings generally understood by those of ordinary skill in the art of the present application.

It should be noted that the terms used herein are merely for describing specific embodiments, and are not intended to limit exemplary embodiments according to the present application. As used herein, unless otherwise explicitly indicated by the context, the singular form is also intended to include the plural form, in addition, it should also be understood that when the terms "include" and/or "comprise" are used in the specification, they indicate features, steps, operations, devices, components and/or their combination.

"Ultrahigh pressure" mentioned in the present invention indicates that the loading pressure of the system can reach 63 MPa.

The present invention will be further illustrated below in conjunction with the drawings and embodiments.

Figure 1:
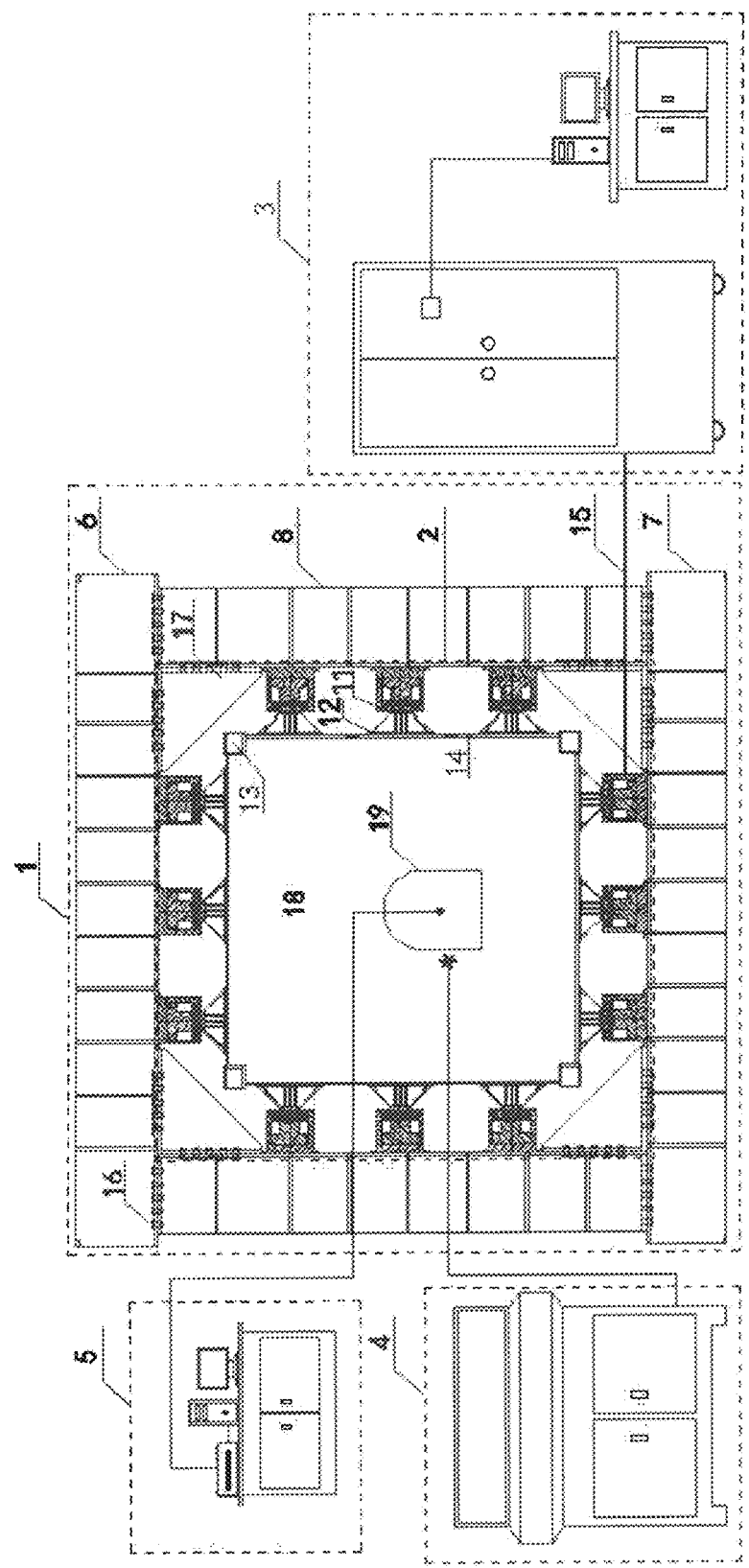
FIG. 1 is a plane design diagram of an overall structure of the present invention.

As shown in FIG. 1, an intelligent numerically-controlled ultrahigh pressure true three-dimensional non-uniform loading/unloading and steady pressure model test system includes a combined bench counterforce device 1, an ultrahigh pressure true three-dimensional non-uniform loading/unloading device 2, an intelligent hydraulic loading/unloading and steady pressure numerical control system 3, an automatic model displacement test system 4 and a high-definition multi-probe peeping system 5. The ultrahigh pressure true three-dimensional non-uniform loading/unloading device 2 is arranged in the combined bench counterforce device 1, and the intelligent hydraulic loading/unloading and steady pressure numerical control system 3 is connected with the ultrahigh pressure true three-dimensional non-uniform loading/unloading device 2 via a high-pressure oil pipe 15. The whole model test system controls the true three-dimensional loading device 2 in a digital servo manner via a loading/unloading instruction input by the intelligent hydraulic loading/unloading and steady pressure numerical control system 3 to carry out ultrahigh pressure true three-dimensional gradient non-uniform loading/unloading and steady pressure control. In the model test process, the automatic model displacement test system 4 automatically acquires the displacement of any part inside a model, and the high-definition multi-probe peeping system 5 observes the excavation deformation and failure status of a model cavern 19 dynamically in real time.

As shown in FIGS. 1-6, the combined bench counterforce device 1 is formed by connecting detachable box-type members, adjustable in size, mainly used for accommodating a test model 18 and used as a counterforce device for loading in test. The size of the combined bench counterforce device 1 can be randomly adjusted according to the model test range, the combined bench counterforce device 1 includes a box-type top beam 6, a box-type bottom beam 7, box-type left and right upright posts 8, a box-type front counterforce wall 9, a box-type rear counterforce wall 10 and other components, and all the components are machined from high-strength steel plates having the thicknesses of 25 mm and connected via high-strength bolts 16, steel corner fittings 17 and tie bars 20. The combined bench counterforce device 1 has the length of 5.05 m, the height of 4.85 m and the thickness of 3.6 m. The net size of the test model 18 is 2.5 m (length) * 2.5 m (height) * 2.0 m (thickness).

In order to control the deformation of the combined bench counterforce device 1, the upper and lower parts of the box-type front counterforce wall 9 and the box-type rear counterforce wall 10 of the combined bench counterforce device 1 are tensioned and strengthened via eight tie bars 20. The combined bench counterforce device 1 adopts a modular combined structure, and the size thereof is variable and can be randomly adjusted according to the size of the test model 18, thus overcoming the defect that most of the existing model test counterforce devices are fixed in size and cannot be flexibly adjusted according to the model test range.

Figure 6:
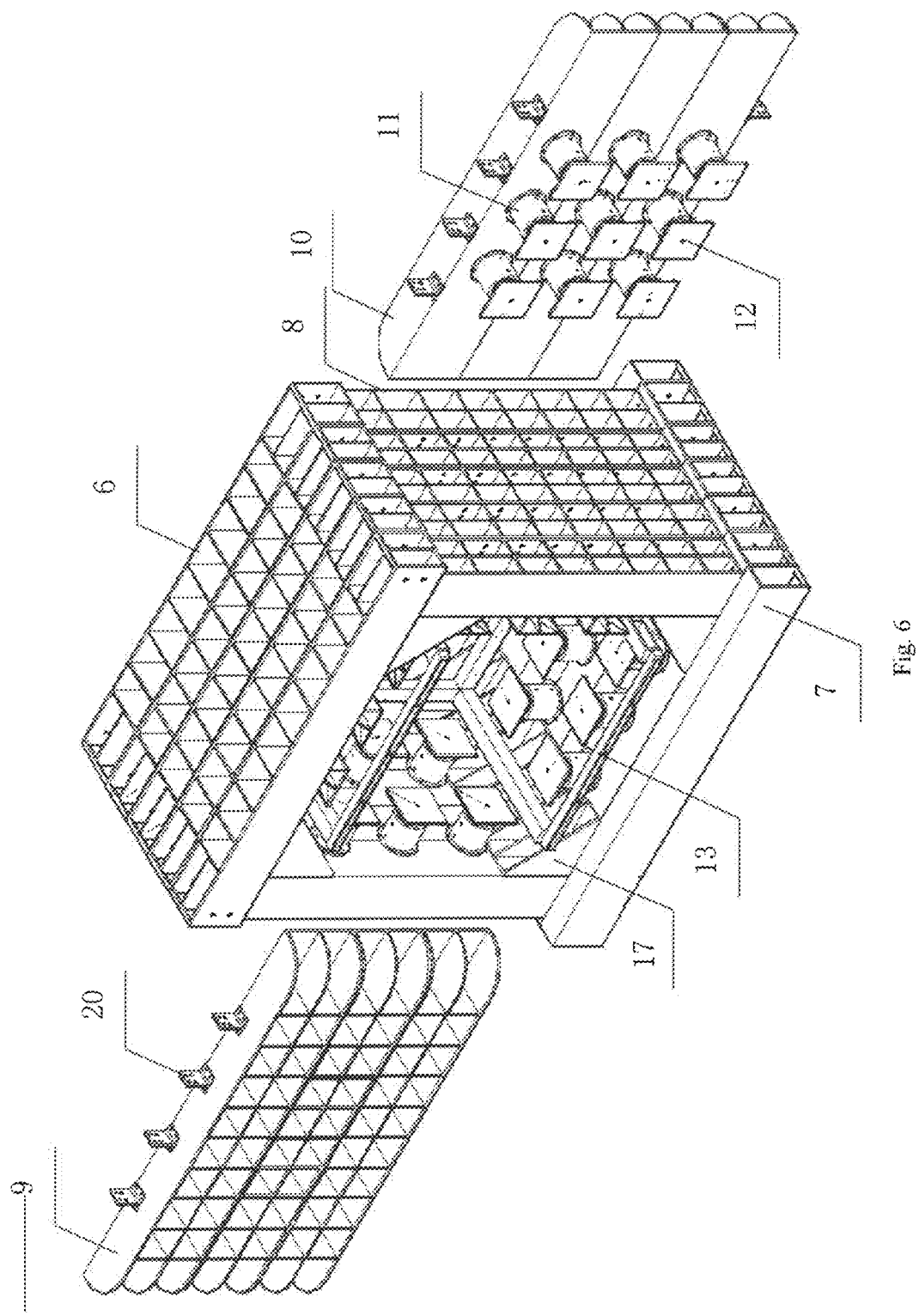
FIG. 6 is an internal three-dimensional design diagram of the combined bench counterforce device of the present invention.
Figure 7:
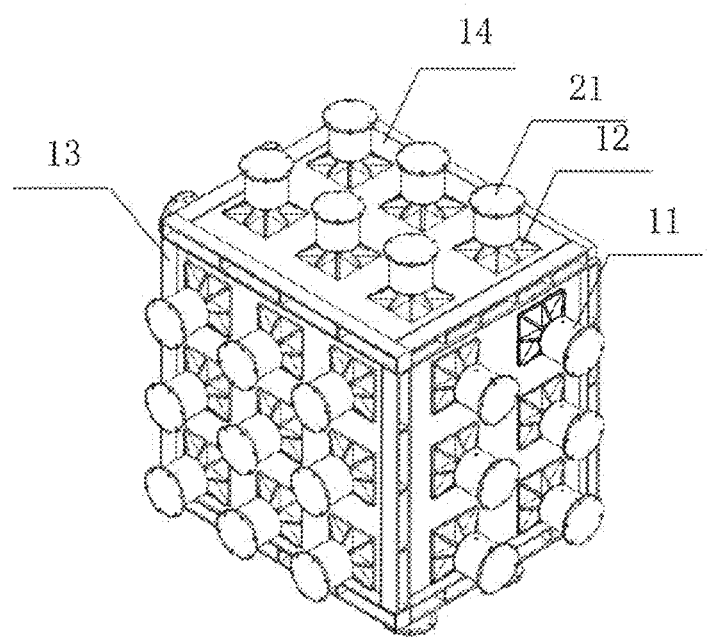
FIG. 7 is a three-dimensional design diagram of an ultrahigh pressure true three-dimensional non-uniform loading/unloading device of the present invention.

As shown in FIGS. 1, 6 and 7, the ultrahigh pressure true three-dimensional non-uniform loading/unloading device 2 is arranged in the combined bench counterforce device 1 and consists of 33 independent loading units which are respectively fixed on the upper, lower, left, right and rear surfaces of the combined bench counterforce device 1 to carry out active true three-dimensional loading, and the front of the model adopts a displacement constrained passive loading mode in order to facilitate cavern excavation.

Six loading units are distributed on each of the upper, lower, left and right surfaces of the model, and nine loading units are distributed on the box-type rear counterforce wall 10. The 33 loading units are divided into eight groups, six loading units in one group are arranged at the top of the model, six loading units in one group are arranged at the bottom of the model, the loading units on the left and right sides of the model are divided into three gradient loading layers from top to bottom, each layer has four loading units constituting one group, and there are totally three groups on the left and right sides; and the loading units on the rear surface of the model are divided into three gradient loading layers from top to bottom, each layer has three loading units constituting one group, and there are totally three groups on the rear surface. The eight groups of loading units respectively carry out independent and synchronous ultrahigh pressure gradient non-uniform loading/unloading via eight oil ways controlled by the intelligent hydraulic loading/unloading and steady pressure numerical control system 3.

Figure 8:
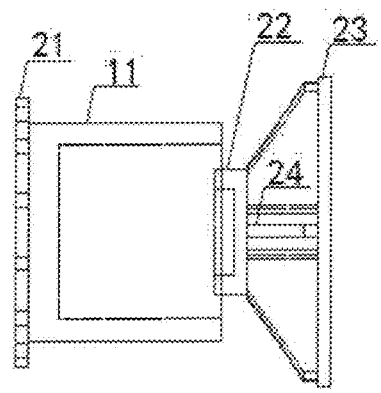
FIG. 8 is a plane design diagram of a force transfer loading unit of the present invention.

As shown in FIGS. 7 and 8, each loading unit includes a hydraulic jack 11 and a bench-type force transfer loading module 12, the rated output of the hydraulic jack 11 is 5000 KN, the diameter of the oil cylinder is 280 mm, and the maximum range is 100 mm. The bench-type force transfer loading module 12 is formed by welding a top plate 22 (length 200 mm, width 200 mm, thickness 30 mm), a bottom plate 23 (length 500 mm, width 500 mm, thickness 30 mm) and eight force transfer reinforcing rib plates 24 having the thicknesses of 25 mm, and the force transfer reinforcing rib plates 24 having the included angles of 45 degrees there between are uniformly distributed between the top plate 22 and the bottom plate 23 at the distance of 110 mm. The rear end of the hydraulic jack 11 is connected with the combined bench counterforce device 1 via a flange plate 21, and the front end of the hydraulic jack 11 is connected with the top plate 22 of the bench-type force transfer loading module 12 via high-strength bolts. The bottom plate 23 of the bench-type force transfer loading module 12 clings to a loading steel plate 14 of the test model 18, thus effectively transferring the output of each loading unit to the surface of the test model 18. The load of the hydraulic jack 11 can be uniformly applied to the test model 18 by using the bench-type force transfer loading module 12 and the combined bench counterforce device 1.

As shown in FIGS. 1, 6 and 7, in order to ensure that the test model is not disturbed by the adjacent load in the true three-dimensional loading process, a three-dimensional loading guide frame 13 is arranged close to the exterior of the test model 18, and the three-dimensional loading guide frame 13 is arranged at the junction of the adjacent loading surfaces of the test model 18 and formed by welding 12 stainless steel square tubes having the cross section in the size of 100 mm * 100 mm. The model loading steel plate 14 clings to the surface of the test model 18 and is embedded into the three-dimensional loading guide frame 13 a certain depth, thus ensuring that the test model is not disturbed by the adjacent loading surface in respective loading direction. The model loading steel plate 14 is provided with test cable lead holes at predetermined positions.

Figure 2:
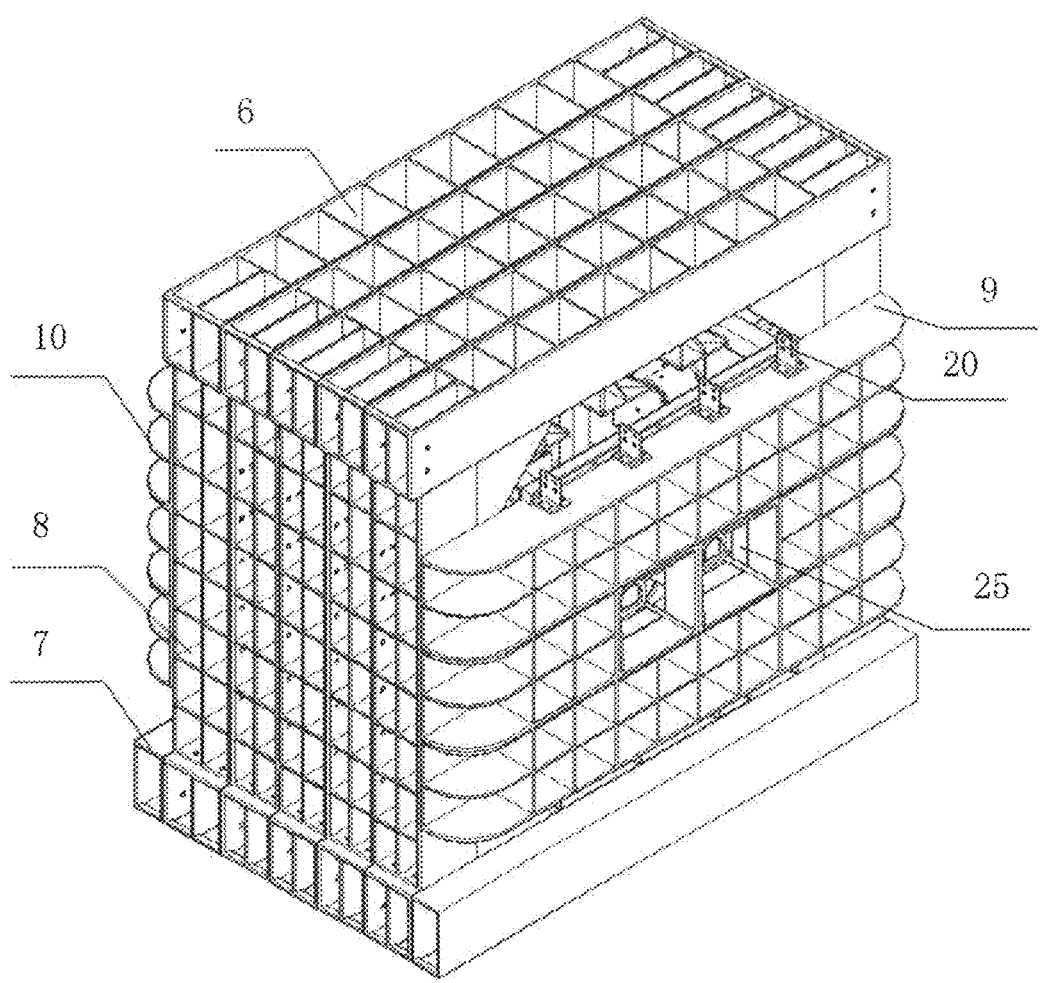
FIG. 2 is a three-dimensional design diagram of a combined bench counterforce device of the present invention.
Figure 3:
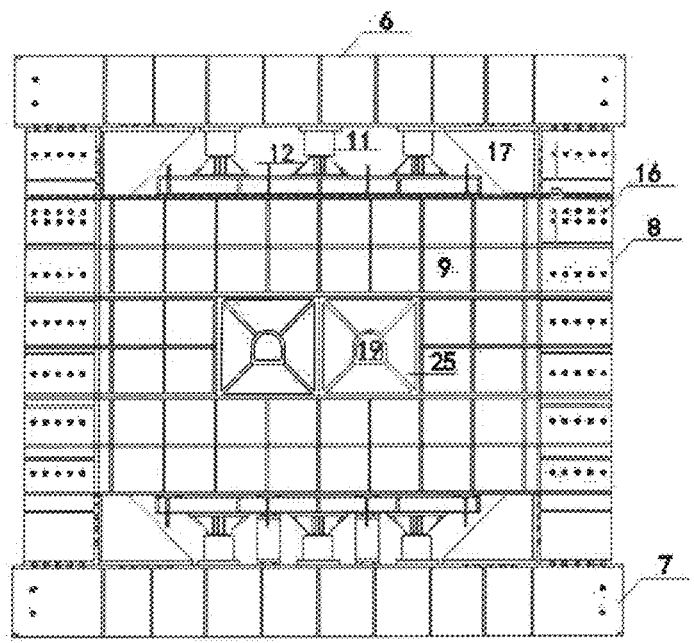
FIG. 3 is a front plane diagram of the combined bench counterforce device of the present invention.
Figure 4:
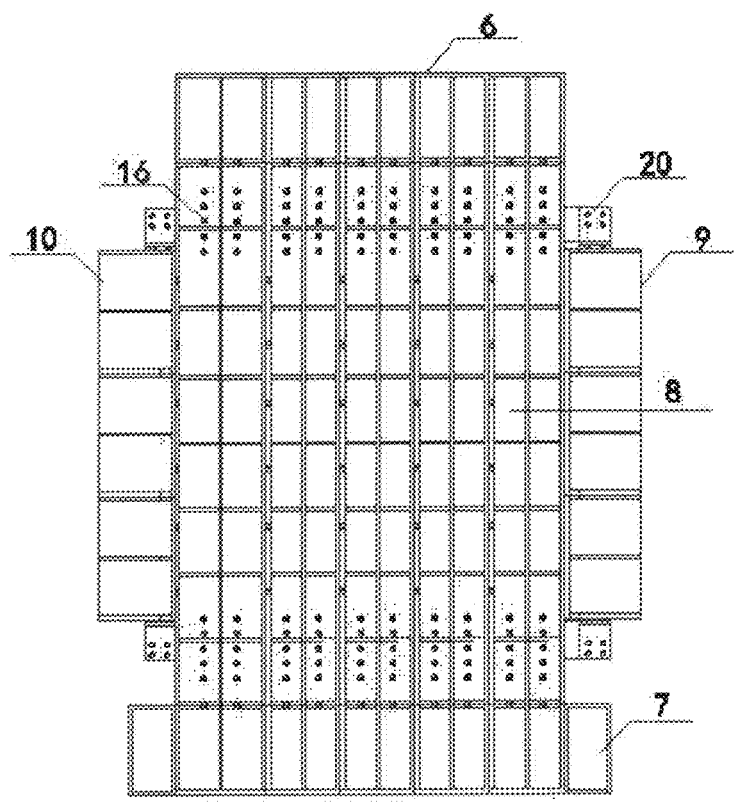
FIG. 4 is a side plane diagram of the combined bench counterforce device of the present invention.
Figure 5:
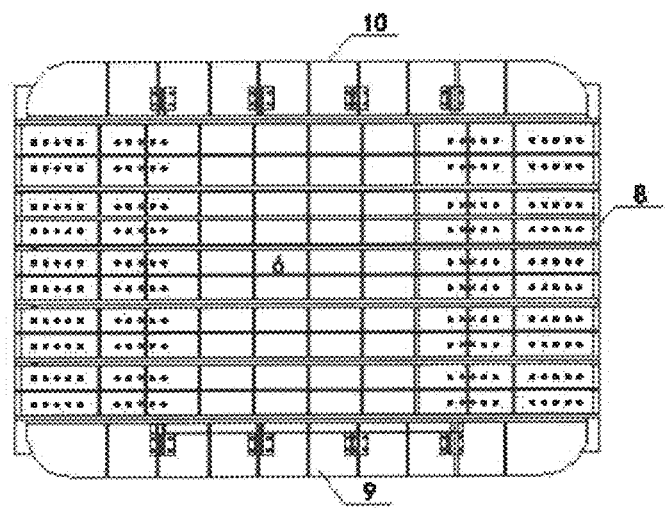
FIG. 5 is a top-view plane diagram of the combined bench counterforce device of the present invention.
Figure 9:
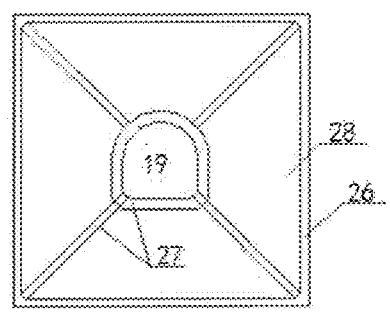
FIG. 9 is a plane design diagram of an excavation window of the present invention.

As shown in FIGS. 2, 3 and 9, a cavern excavation window 25 is arranged in the middle of the box-type front counterforce wall 9 of the combined bench counterforce device 1 and connected with the box-type front counterforce wall 9 of the combined bench counterforce device 1 via high-strength bolts, and the cavern excavation window 25 has the length of 750 mm, the width of 750 mm and the thickness of 500 mm. The cavern excavation window 25 is mainly composed of a division plate 26, a steel frame 27, a toughened glass panel 28 and a model cavern excavation opening 19 cut on the toughened glass panel 28. By detaching and replacing the toughened glass panel 28 containing the cavern 19 in different shape and size, the model cavern 19 can be conveniently excavated and the deformation and failure phenomena of the cavern can be conveniently observed.

Figure 10:
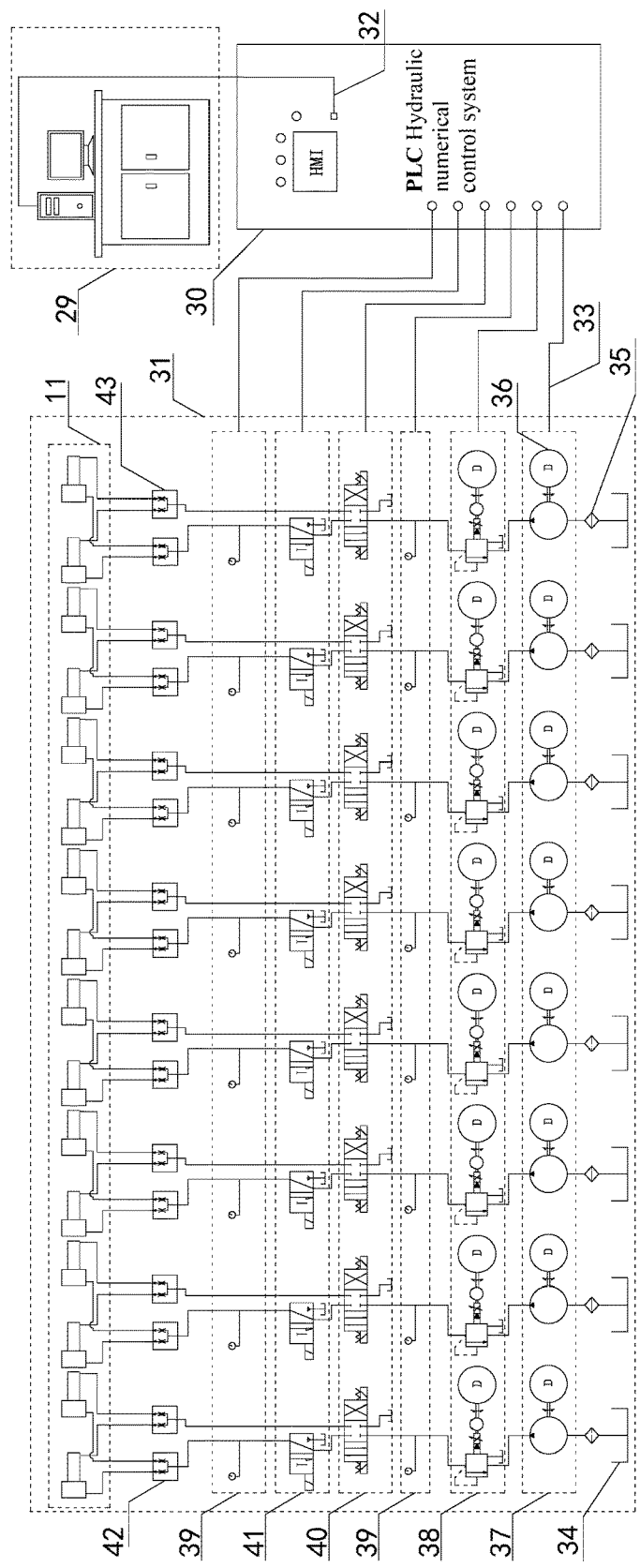
FIG. 10 is a design diagram of an oil way of the system of the present invention.

As shown in FIG. 10, the intelligent hydraulic loading/unloading and steady pressure numerical control system 3 is composed of a PC monitoring system 29, a PLC hydraulic numerical control system 30 and an ultrahigh pressure execution system 31. The PC monitoring system 29 is connected with the PLC hydraulic numerical control system 30 via a network cable 32, and the PLC hydraulic numerical control system 30 is connected with the ultrahigh pressure execution system 31 to form full closed-loop control on pressure. Hydraulic oil in the oil way enters the hydraulic jack 11 from the oil tank 34 via the oil filter 35, the oil pump 37, the step overflow valve 38, the O-shaped three-position four-way electromagnetic reversing valve 40, the electromagnetic ball valve pressure retaining valve 41 and the synchronous valve 42, and then enters the O-shaped three-position four-way electromagnetic reversing valve 40 via a collecting valve 43 to form back flow. The step overflow valve 38 is used for adjusting the pressure of the oil way; the O-shaped three-position four-way electromagnetic reversing valve 40 is used for controlling the flow direction of the oil way; the electromagnetic ball valve pressure retaining valve 41 plays a role in retaining the pressure; and the synchronous valve 42 is used for ensuring that different hydraulic jacks 11 on the same way realize synchronous loading. The pressure adjustment process of the step overflow valve 38 is realized in such a way that a step motor 36 drives the valve core of the step overflow valve 38 to advance or retreat, and when the step motor 36 drives the valve core to advance, the pressure of the oil way is reduced, otherwise, the pressure of the oil way is increased. The start pressure of the system can be reduced to 0MPa via variable frequency debugging of a step overflow valve drive system 48 in combination with the stepless speed adjustment of the step motor 36 to realize zero pressure start. The PLC hydraulic numerical control system 30 can adjust the pressure change rate of the step overflow valve 38 to realize cyclic loading/unloading of the system. When the oil pressure of the hydraulic jack 11 is changed, the PLC hydraulic numerical control system 30 controls the step overflow valve 38 in a servo manner to increase or reduce the pressure to realize instantaneous pressure supplement, so that the loading system is kept in a steady pressure state.

The ultrahigh pressure execution system 31 is divided into eight oil ways which are mutually independent and parallel, each oil way separately controls a group of loading units of the ultrahigh pressure true three-dimensional non-uniform loading/unloading device 2, and the oil ways run independently and do not disturb each other. In the test process, the eight independent oil ways respectively carry out loading according to the actual geostress, wherein the top oil way carries out loading according to $\sigma_{top}=\gamma h_{top}$, $h_{top}$ is the actual buried depth of the top stratum of the model, the bottom oil way carries out loading according to $\sigma_{bottom}=\gamma h_{bottom}$, $h_{bottom}$ is the actual buried depth of the bottom stratum of the model, the three gradient loading layers of the sides and the rear surface of the model respectively carry out loading according to $\sigma_{gradient1}=\kappa\gamma h_{gradient1}$, $\sigma_{gradient2}=\kappa\gamma h_{gradient2}$ and $\sigma_{gradient3}=\kappa\gamma h_{gradient3}$, in which $\gamma$ is the volume weight of a rock mass, $\kappa$ is the side pressure coefficient of the geostress, and $h_{gradient}$ is the actual buried depth of the stratum at each gradient loading layer. Thus, true three-dimensional gradient non-uniform loading changing with the depth is realized.

Figure 11:
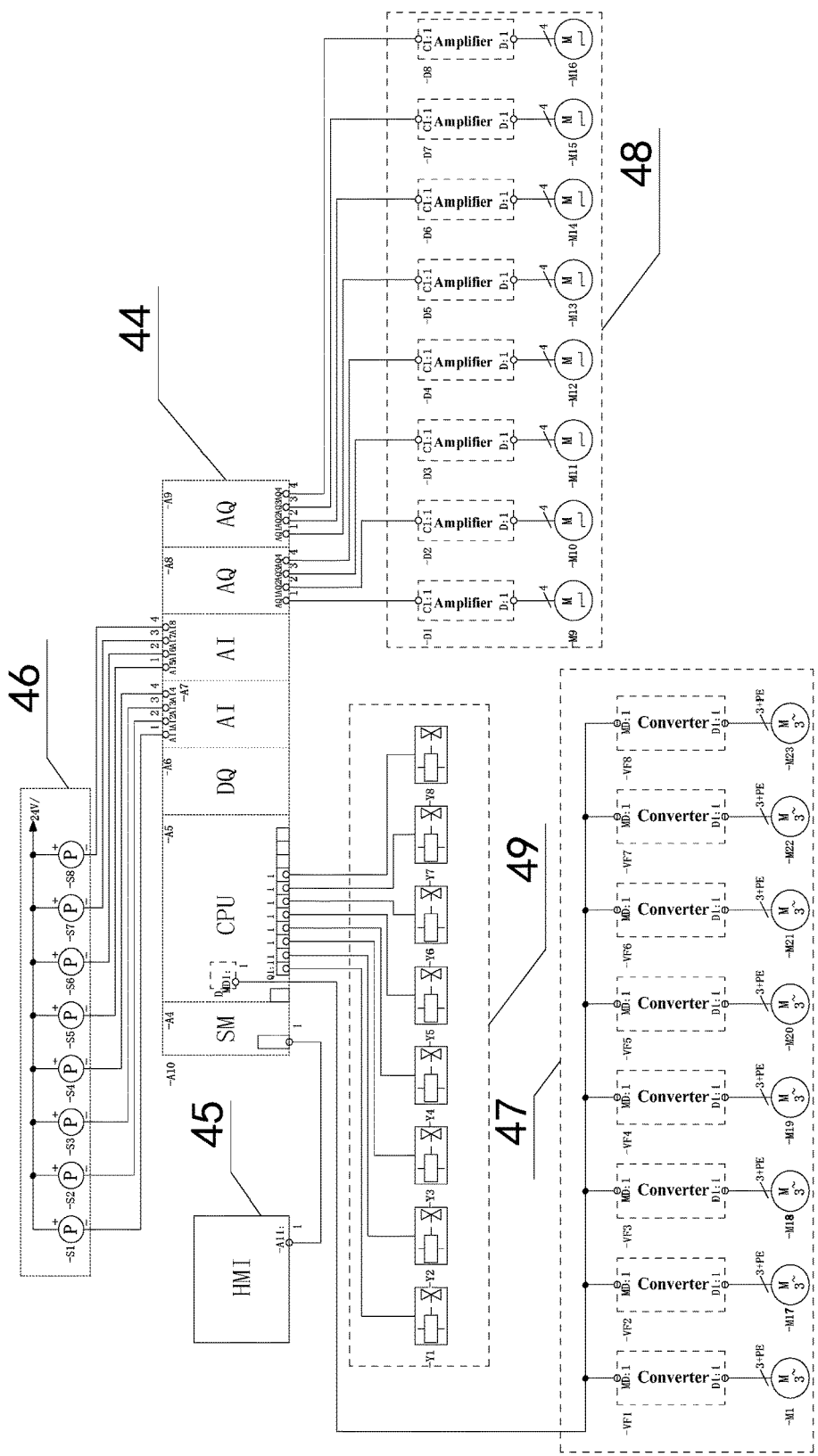
FIG. 11 is a design diagram of circuits of the system of the present invention.

As shown in FIG. 11, the PLC hydraulic numerical control system 30 includes a human-machine interface (HMI) 45, a programmable controller 44, a sensor system 46, a variable frequency oil pump drive system 47, a step overflow valve drive system 48 and an electromagnetic valve drive system 49. Firstly, an operator inputs a loading/unloading instruction via the human-machine interface (HMI) 45, and the programmable controller 44 serving as a central processing unit converts the input loading/unloading instruction into an electrical signal and transmits the electrical signal to the variable frequency oil pump drive system 47, the step overflow valve drive system 48 and the electromagnetic valve drive system 49 respectively; then the variable frequency oil pump drive system 47 controls the oil pump 37 to pump the hydraulic oil into the oil ways, and the step overflow valve drive system 48 controls the step motor 36 to drive the valve core of the step overflow valve 38 to advance or retreat, thus reducing or increasing the pressure of the oil ways. The electromagnetic valve drive system 49 controls opening or closing of the O-shaped three-position four-way electromagnetic reversing valve 40 and the electromagnetic ball valve pressure retaining valve 41 to realize division and pressure retention of the oil ways; and finally, the sensor system 46 feeds the detected oil way pressure information back to the programmable controller 44 in time to process the oil way pressure information into a digital pressure signal, and the digital pressure signal is displayed on the HMI 45 dynamically in real time.

Figure 12:
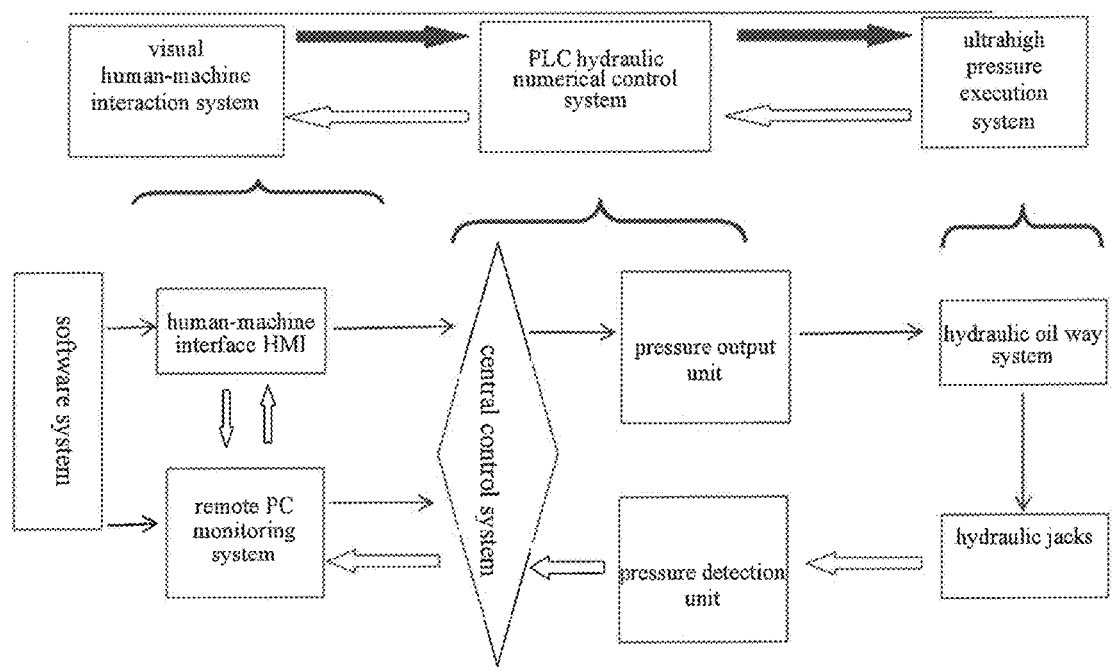
FIG. 12 is a flow diagram of pressurized control of the present invention.

As shown in FIG. 12, the pressure control flow of the intelligent hydraulic loading/unloading and steady pressure numerical control system is as follows: the operator inputs a loading/unloading instruction via the HMI 45 or the PC monitoring system 29 of the visual human-machine interaction system, and the visual human-machine interaction system converts the loading/unloading instruction into a digital pressure signal and transmits the digital pressure signal to the PLC hydraulic numerical control system 30. The PLC hydraulic numerical control system 30 receives the digital pressure signal, the central control unit of the PLC hydraulic numerical control system converts the digital pressure signal into an electrical signal, then the electrical signal is transmitted to the ultrahigh pressure execution system 31 via the pressure output unit, and the ultrahigh pressure execution system 31 receives the electrical signal to control start or shutdown of the step motor, advancing or retreating of the valve core of the step overflow valve and operation of various electrical elements, thus realizing the loading, unloading and pressure retaining functions of the hydraulic jacks. The pressure detection unit of the PLC hydraulic numerical control system 30 detects the pressure value of the oil way dynamically in real time and feeds the pressure change information to the central control unit timely to process the pressure change information into a digital signal, the digital signal is displayed on the visual human-machine interaction system dynamically in real time, and the loading history is stored in the PC monitoring system 29.

Figures 13, 14:
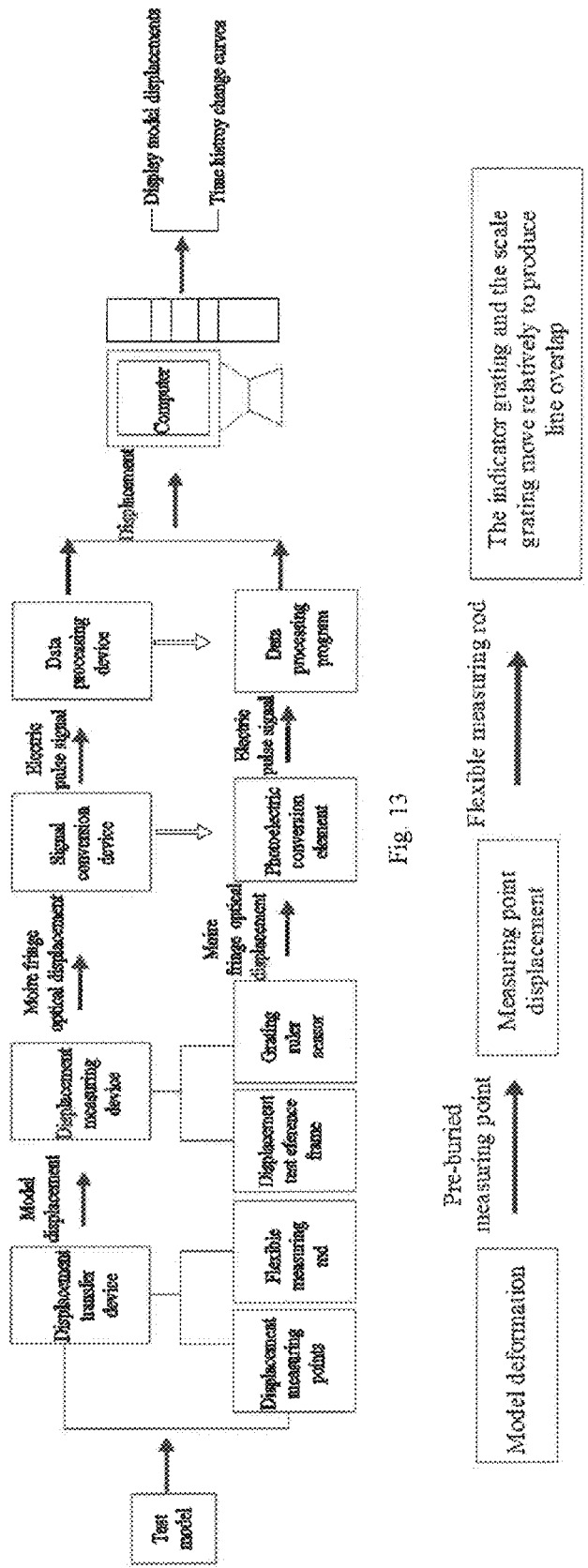
FIG. 13 is a work flow diagram of an automatic model displacement test system of the present invention.
FIG. 14 is a principle diagram of photoelectric conversion of the automatic model displacement test system of the present invention.

As shown in FIG. 13, the automatic model displacement test system 4 is mainly composed of a displacement transfer device, a displacement measuring device, a signal conversion device, a data processing device and a computer system. The basic work flow of the automatic model displacement test system 4 is: when the model produces a displacement, the displacement transfer device transfers the displacement of a model measuring point to the displacement measuring device first via a flexible measuring rod, and the displacement measuring device converts the displacement of the model measuring point into a moire fringe displacement via a grating ruler sensor thereof; then, the signal conversion device converts the moire fringe displacement into an electric pulse signal via a photoelectric conversion element thereof and transmits the electric pulse signal to the data processing device; and finally, the data processing device receives the electric pulse signal and converts the electric pulse signal into a digital signal, then the displacement of the model is calculated out and stored and displayed on the computer in real time, meanwhile, a model displacement time-history curve is automatically generated for a tester to dynamically observe and monitor the displacement of the model, so that digital, visual and intelligent automatic measurement of the displacement of the model is realized.

The displacement measuring device is a grating ruler sensor 54, and it is a high-precision optical test element for measuring the displacement of the model measuring point by using moire fringe shift, and is composed of an indicator grating and a scale grating; the signal conversion device is composed of a photoelectric conversion element, and is used for converting the optical signal of moire fringe shift into an electric pulse signal; the data processing device adopts a programmable controller, stores the pre-written program into a memory of the central control unit, and is used for receiving the electric pulse signal output by the signal conversion device, converting the electric pulse signal into a digital signal, then calculating the displacement of the model, storing and displaying the displacement on the computer in real time, and automatically generating a model displacement time-history change curve.

As shown in FIG. 14, the automatic model displacement test system 4 realizes automatic detection of model displacement via a photoelectric conversion technology, and the photoelectric conversion principle for displacement test is: the deformation of the test model 18 drives displacement of a pre-buried measuring point, the displacement of the measuring point is transferred to the grating ruler sensor of the displacement measuring device via the flexible measuring rod of the displacement transfer device, thus, the indicator grating and the scale grating of the grating ruler sensor move relatively, and when the indicator grating and the scale grating produce a relative displacement, the lines of the indicator grating and the scale grating are overlapped to produce black and white moire fringes, wherein the movement of the moire fringes corresponds to the relative displacement between the indicator grating and the scale grating. For the movement of the moire fringes, the optical signal can be converted into an electric pulse signal via the photoelectric conversion element, the electric pulse signal is converted into digital displacement via the data processing device, and the digital displacement is finally automatically stored in the industrial control computer and synchronously displayed in real time.

Figure 15:
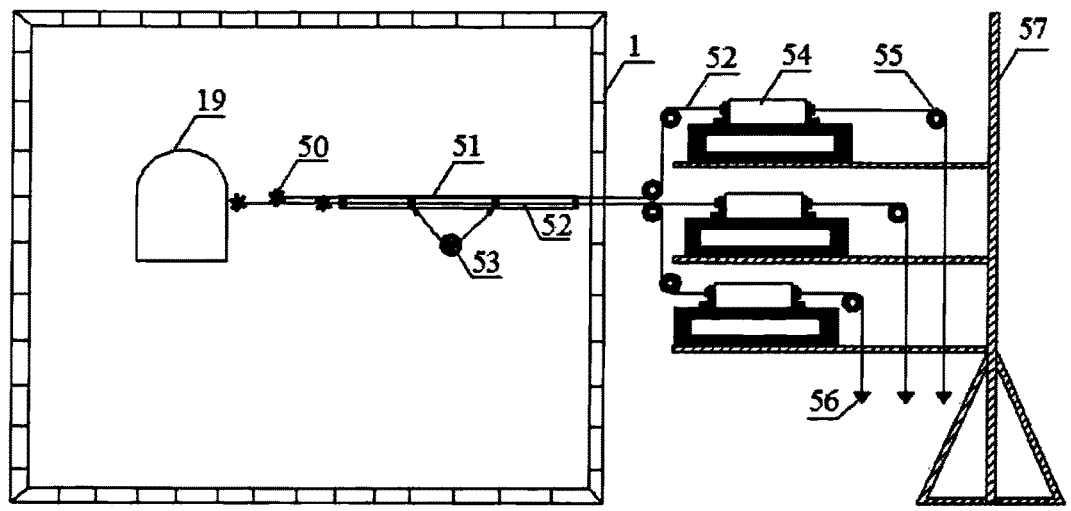
FIG. 15 is a connection diagram of a displacement transfer device and a displacement measuring device of the present invention.

As shown in FIG. 15, the displacement transfer device includes a displacement measuring point 50, a PVC sleeve 51, a flexible thin wire rope 52, an anti-friction positioning disc 53, a displacement transfer pulley 55 and a self-balancing hammer 56. The displacement measuring point 50 is a gear-like pre-buried object made of manganese steel and having small size. A displacement measuring rod is composed of the PVC sleeve 51, the flexible thin wire rope 52 and the anti-friction positioning disc 53. The displacement measuring rod is made of the flexible thin wire rope 52 that is deformation-free in the axial direction and can be bent randomly, the diameter of the wire rope is 0.5 mm, the wire rope is formed by twisting 49 strands of thin wires, and the transparent PVC sleeve 51 having the inner diameter of the 4 mm and the outer diameter of 6 mm is sleeved outside the thin wire rope for protection. The manufacturing method of the displacement measuring rod is: fixing the flexible thin wire rope 52 and the displacement measuring point 50 by adopting AB glue, threading the flexible thin wire rope 52 into a positioning hole (the positioning hole is used for isolating the flexible thin wire rope 52, so that the flexible thin wire rope 52 can move axially in a fixed passage without contacting other flexible thin wire rope 52 or contacting the PVC sleeve 51, and this can ensure that the flexible thin wire rope 52 transfers the displacement of the measuring point with very high precision) of the anti-friction positioning disc 53, and fixing the anti-friction positioning disc 53 threaded with the flexible thin wire rope 52 into the transparent PVC sleeve 51, thus forming the displacement measuring rod. During test, the displacement measuring point 50 is embedded into the model 18, one end of the flexible thin wire rope 52 of the displacement measuring rod is connected with the displacement measuring point 50, the other end is led out of the reserved cable hole of the combined bench counterforce device 1, passes through the displacement transfer pulley 55 and is connected with the grating ruler sensor 54 of the displacement measuring device, and the flexible thin wire rope 52 is tensioned by adopting the self-balancing hammer 56 at the tail end of the wire rope 52.

Figure 16:
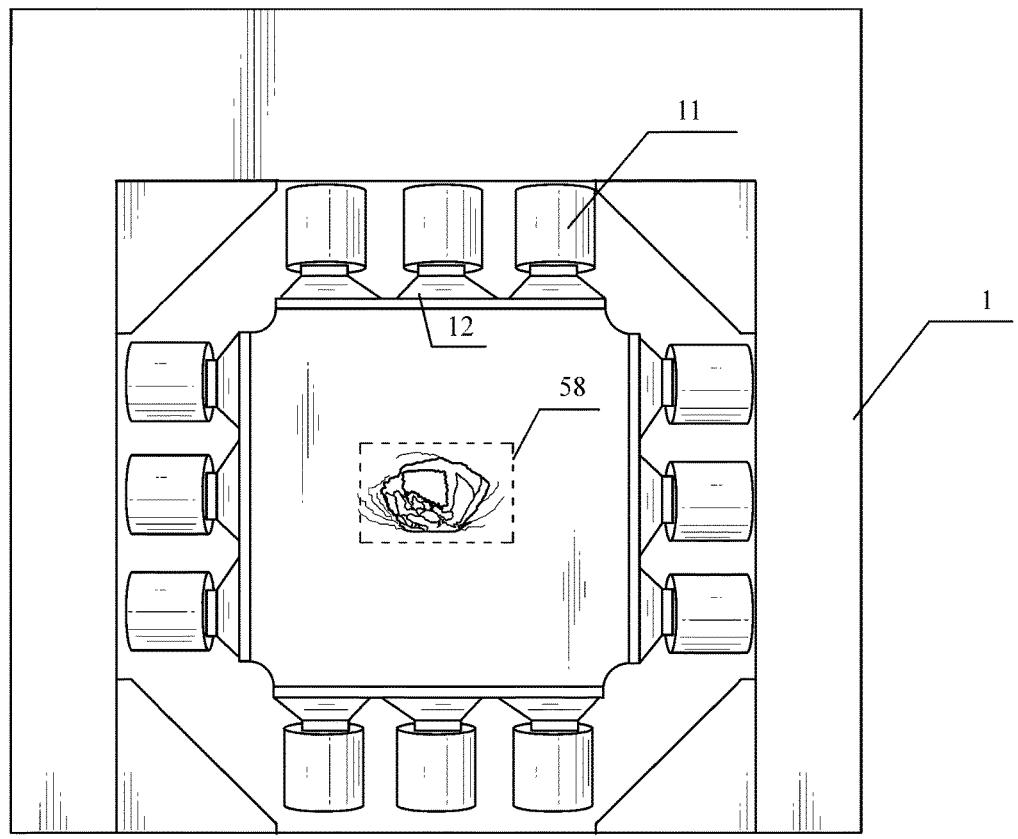
FIG. 16 is a panoramic photo of collapse failure model test of a deep buried carbonatite reservoir paleocave.
Figure 17:
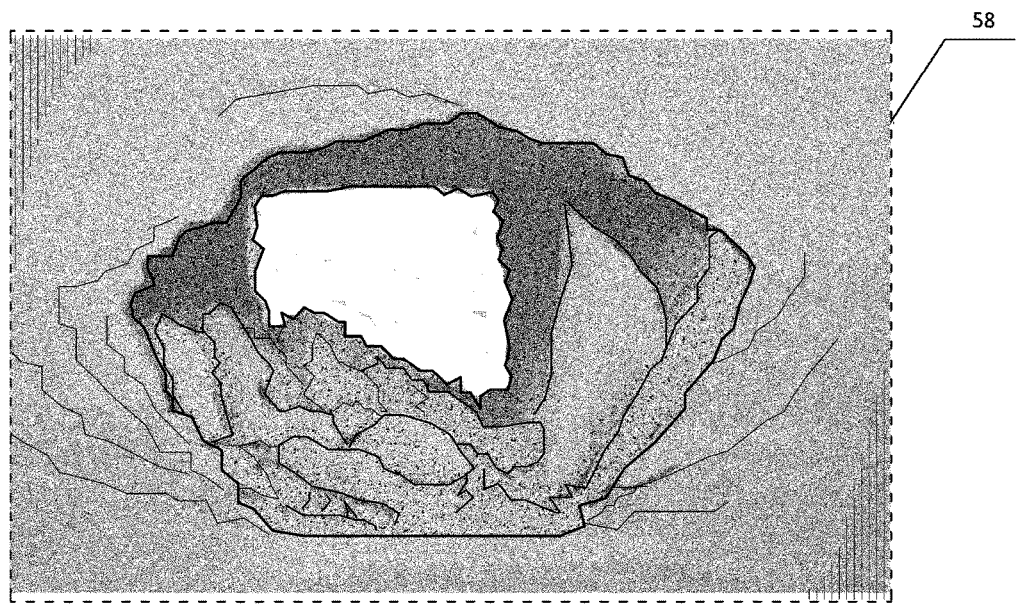
FIG. 17 is a close-shot photo of collapse failure of the deep buried carbonatite reservoir paleocave.
Figure 18:
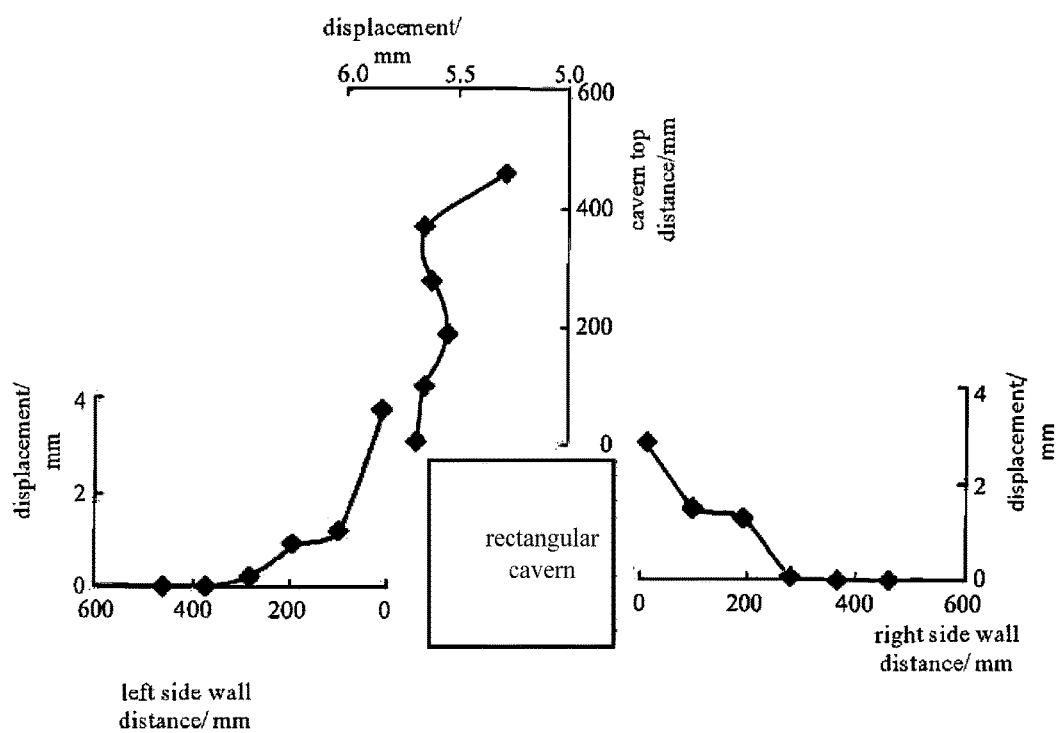
FIG. 18 is a displacement distribution diagram of model cavern circumference after the paleocave collapse.
Figure 19:
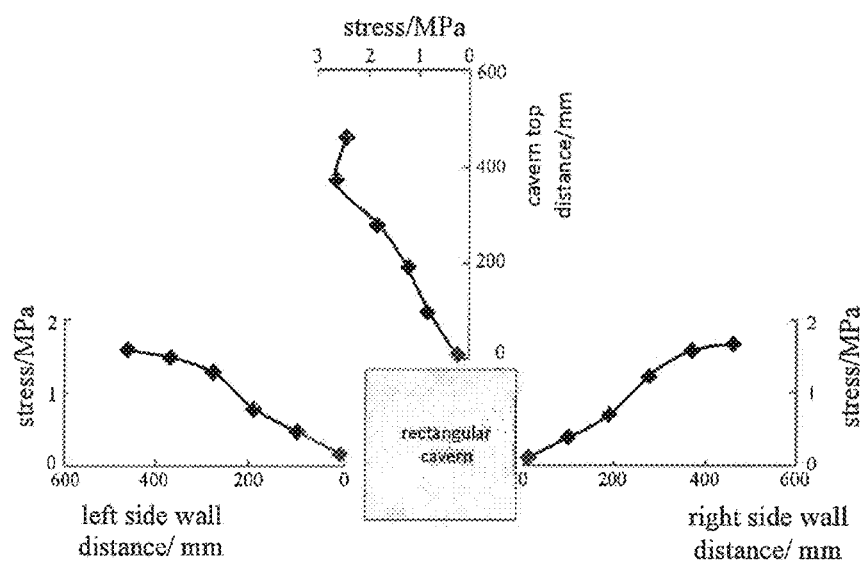
FIG. 19 is a radial stress distribution diagram of model cavern circumference after the paleocave collapse.

The present invention is applied to three-dimensional geomechanical model test on the collapse failure process of a deep buried carbonatite reservoir paleocave buried under nearly 6000 m, FIG. 16 is a panoramic photo of the collapse failure model test of a deep buried carbonatite reservoir paleocave, FIG. 17 is a close-shot photo of the collapse failure of the deep buried carbonatite reservoir paleocave, FIG. 18 is a displacement distribution diagram after the model cavern collapse, and FIG. 19 is a radial stress distribution diagram after the model cavern collapse.

It can be known from the analysis on FIGS. 16 and 17 that, because the vertical stress of the cavern is greater than the horizontal tectonic stress, the collapse failure mode 58 of the reservoir paleocavesis is tensile shear failure, the side wall fracture surface of the cavern is approximately parallel to the vertical maximum principal stress direction, and a V-shaped tensile shear failure surface is finally produced.

It can be known from the analysis on FIG. 18 that the top displacement of the cavern is relatively large and uniform, indicating that the whole top plate of the cavern moves down in the forming process. The displacements of the left and right side walls of the cavern are gradually reduced with the increase of the distances away from the cavern wall, wherein displacements approaching measuring points of the cavern wall are relatively maximum, indicating that the position approaching the cavern wall is a most serious failure area of the cavern under the high geostress deep buried condition. With the extension out of the cavern, the displacement of measuring points being 2.3 times cavern span away from the cavern wall is attenuated to 0, indicating that the position is beyond the influence coverage of cavern failure, wherein the maximum influence coverage of cavern collapse failure is 2.3 times cavern span.

It can be known from the analysis on FIG. 19 that, the closer to the cavern wall, the more serious the radial stress release of the cavern, the radial stress of measuring points being 2.3 times cavern span away from the cavern wall is substantially not changed, indicating that this position is beyond the influence coverage of cavern failure, and the maximum influence coverage of the cavern collapse failure is 2.3 times cavern span.

The engineering application shows: the present invention reproduces the collapse failure process of the deep buried carbonatite reservoir paleocave in a panoramic manner, obtains the nonlinear deformation characteristic and the stress change rule in the process of the paleocave collapse failure, reveals the collapse failure mode 58 of the reservoir paleocaves, and provides an important experimental basis for optimizing the oil exploitation technology of the carbonatite reservoir paleocave, and the practical engineering application powerfully validates the reliability of the present invention. The present invention has an important application prospect in simulating the nonlinear deformation failure mechanism of deep buried underground caverns of energy, traffic, hydropower, mines and so on.

Although the specific embodiments of the present invention are described above in combination with the accompanying drawings, the protection scope of the present invention is not limited thereto. It should be understood by those skilled in the art that various modifications or variations could be made by those skilled in the art based on the technical solution of the present invention without any creative effort, and these modifications or variations shall fall into the protection scope of the present invention.

The invention claimed is:

1. An auto-controlled pressure three-dimensional non-uniform loading/unloading and steady pressure model test system, comprising:
   a counterforce device;
   a pressure three-dimensional non-uniform loading/unloading device;
   a hydraulic loading/unloading and steady pressure automatic control system;
   an automatic model displacement test system; and
   a multi-probe peeping system, wherein the pressure three-dimensional non-uniform loading/unloading device is automatically controlled via an input instruction of the hydraulic loading/unloading and steady pressure automatic control system to carry out pressure three-dimensional gradient non-uniform loading/unloading and steady pressure control; the automatic model displacement test system automatically acquires displacement of any part inside a test model; and the multi-probe peeping system observes a cavern excavation deformation and failure process of a cavern located within the test model dynamically in real time;
   wherein the pressure three-dimensional non-uniform loading/unloading device comprises 33 loading units which are respectively fixed on upper, lower, left, right and rear surfaces of the counterforce device to carry out active three-dimensional loading, and a front of the test model adopts a displacement constraining passive loading mode, and
   wherein the 33 loading units are included and divided in eight groups, six loading units in a first group of the eight groups are arranged at a top of the test model, six loading units in a second group of the eight groups are arranged at a bottom of the test model, and six loading units from top to bottom with each group of the three groups including four loading units; and nine loading units are arranged on a rear surface of the test model and divided into three groups from top to bottom with each group including three loading units.

2. The auto-controlled pressure three-dimensional non-uniform loading/unloading and steady pressure model test system according to claim 1, wherein the counterforce device is formed by connecting detachable members each having a square cross section, adjustable in size, used for accommodating the test model and used as a counterforce device for loading in test; the counterforce device comprises a bottom beam having a square cross section; a top beam having a square cross section, a left upright post having a square cross section, a right upright post having a square cross section, a front counterforce wall member having a square cross section and a rear counterforce wall member having a square cross section; the bottom beam and the top beam are distributed up and down and connected with each other via the left and right upright posts to form a rectangular frame structure, the front counterforce wall member and the rear counterforce member are arranged in the front and the back of the rectangular frame, and the whole counterforce device is combined via a connecting device.

3. The auto-controlled pressure three-dimensional non-uniform loading/unloading and steady pressure model test system according to claim 2, wherein a transparent excavation window is arranged in the middle of the front counterforce wall member and comprises a steel frame and a glass panel, and a cavern excavation window is arranged in the center of the glass panel.

4. The auto-controlled pressure three-dimensional non-uniform loading/unloading and steady pressure model test system according to claim 1, wherein the eight groups of loading units respectively carry out independent and synchronous non-uniform loading/unloading via eight oil ways controlled by the hydraulic loading/unloading and steady pressure automatic control system.

5. The auto-controlled pressure three-dimensional non-uniform loading/unloading and steady pressure model test system according to claim 1, wherein each loading unit includes a hydraulic jack and a force transfer loading module; the bottom of the force transfer loading module is coupled to a loading steel plate on the surface of the test model, the top of the force transfer loading module is connected with the front end of the hydraulic jack via a connecting device, and the rear end of the hydraulic jack is connected to the inner wall of the counterforce device via a second device; and the load of the hydraulic jack is uniformly applied to the test model by using the bench-type force transfer loading module and the counterforce device.

6. The auto-controlled pressure three-dimensional non-uniform loading/unloading and steady pressure model test system according to claim 1, wherein a loading guide frame device is arranged juxtapose to the exterior of the test model, and the loading guide frame device is formed by welding stainless steel square tubes; and before loading, a loading steel plate of the test model abuts the surface of the test model and is embedded into the loading guide frame device at a predetermined depth.

7. The auto-controlled pressure three-dimensional non-uniform loading/unloading and steady pressure model test system according to claim 1, wherein the hydraulic loading/unloading and steady pressure automatic control system comprises a visual human-machine interaction system, a PLC hydraulic system and pressure execution system; the visual human-machine interaction system transmits and receives information to and from the PLC hydraulic system; and the PLC hydraulic system transmits and receives information to and from the pressure execution system.

8. The auto-controlled pressure three-dimensional non-uniform loading/unloading and steady pressure model test system according to claim 7, wherein the visual human-machine interaction system includes a human-machine interface (HMI), a PC monitoring system and a software system; the PLC hydraulic system includes a central control unit, a pressure output unit and a pressure detection unit; the pressure execution system includes a hydraulic oil way system and a hydraulic jack; the software system is installed on the HMI and the PC monitoring system, and the PC monitoring system transmits information to the central control unit and the HMI; the HMI also transmits information to the central control unit, the central control unit controls the pressure output unit, the pressure output unit controls the hydraulic oil way system, and the hydraulic oil way system controls the hydraulic jack; the pressure detection unit detects pressure information of the hydraulic jack and feeds the pressure information back to the central control unit, the central control unit processes the pressure information into digital pressure information, and synchronously transmits the digital pressure information to the HMI or the PC monitoring system, and the pressure information is displayed on the HMI or the PC monitoring system.

9. The auto-controlled pressure three-dimensional non-uniform loading/unloading and steady pressure model test system according to claim 8, wherein the hydraulic oil way system includes a step motor, an oil pump, a step overflow valve, an O-shaped three-position four-way electromagnetic reversing valve, an electromagnetic ball valve pressure retaining valve and a synchronous valve; the step overflow is configured to adjust the pressure of the oil ways, the O-shaped three-position four-way electromagnetic reversing valve is configured to control the flow direction of the oil ways, the electromagnetic ball valve pressure retaining valve is configured to retain the pressure in the oil ways, and the synchronous valve is configured for synchronous loading; the step motor starts the oil p ump to pump hydraulic oil into the oil ways, the hydraulic oil enters the step overflow valve, and the PLC hydraulic system controls the step motor according to the pressure information detected by the pressure detection unit in real time to adjust the valve core of the step overflow valve to advance or retreat to reduce or increase the pressure of the oil ways, thus completing a loading-unloading process; and when the pressure of the hydraulic oil way system is changed, the PLC hydraulic numerical control system controls the step overflow valve in a manner to increase or reduce the pressure in the respective oil way to realize instantaneous pressure supplement, and the electromagnetic ball valve pressure retaining valve keeps the loading system in a steady pressure state; in addition, the start pressure of the hydraulic oil way system is reduced to 0MPa via variable frequency debugging of the step overflow valve in combination with stepless speed adjustment of the step motor to realize zero pressure start.

10. The auto-controlled pressure three-dimensional non-uniform loading/unloading and steady pressure model test system according to claim 1, wherein the automatic model displacement test system comprises a displacement transfer device, a displacement measuring device, a signal conversion device, a data processing device and a computer system; the displacement transfer device detects the displacement of the test model; the displacement measuring device transmits the displacement information to the signal conversion device, the signal conversion device transmits information to the data processing device, and the data processing device transmits information to the computer system.

11. The auto-controlled pressure three-dimensional non-uniform loading/unloading and steady pressure model test system according to claim 10, wherein when the test model produces a displacement, the displacement transfer device transfers the displacement of a model measuring point to the displacement measuring device via a flexible measuring rod, and the displacement measuring device converts the displacement of the test model measuring point into a moire fringe displacement via a grating ruler sensor, the signal conversion device converts the moire fringe displacement into an electric pulse signal via a photoelectric conversion element and transmits the electric pulse signal to the data processing device; the data processing device receives the electric pulse signal and converts the electric pulse signal into a digital signal, then model displacements are calculated and stored and displayed on the computer system in real time, meanwhile, model displacement time-history curves are automatically generated for a tester to dynamically observe and monitor the displacement of the test model, so that digital and visual automatic measurement of the displacement of the test model is realized.

12. The auto-controlled pressure three-dimensional non-uniform loading/unloading and steady pressure model test system according to claim 1, wherein the multi-probe peeping system comprises a plurality of probes, a camera control panel, a data storage box and a liquid crystal display; the plurality of probes are arranged at any inner or outer part of the cavern; and an acquired video is displayed in the liquid crystal display in real time and automatically stored in a data storage.

13. An auto-controlled pressure true three-dimensional non-uniform loading/unloading and steady pressure model test system, comprising: a counterforce device; a pressure three-dimensional non-uniform loading/unloading device; a hydraulic loading/unloading and steady pressure automatic control system; an automatic model displacement test system; and a multi-probe peeping system, wherein the pressure three-dimensional non-uniform loading/unloading device is automatically controlled via an input instruction of the hydraulic loading/unloading and steady pressure automatic control system to carry out pressure three-dimensional gradient non-uniform loading/unloading and steady pressure control: the automatic model displacement test system automatically acquires displacement of any part inside a test model: and the multi-probe peeping system observes a cavern excavation deformation and failure process of a cavern located within the test model dynamically in real time; and a loading guide frame device is arranged juxtapose to the exterior of the test model, and the loading guide frame device is formed by welding stainless steel square tubes; and before loading, a loading steel plate of the test model abuts the surface of the test model and is embedded into the loading guide frame device at a predetermined depth.

14. An auto-controlled pressure true three-dimensional non-uniform loading/unloading and steady pressure model test system, comprising: a counterforce device; a pressure three-dimensional non-uniform loading/unloading device; a hydraulic loading/unloading and steady pressure automatic control system; an automatic model displacement test system; and a multi-probe peeping system, wherein the pressure three-dimensional non-uniform loading/unloading device is automatically controlled via an input instruction of the hydraulic loading/unloading and steady pressure automatic control system to carry out pressure three-dimensional gradient non-uniform loading/unloading and steady pressure control; the automatic model displacement test system automatically acquires displacement of any part inside the test model; and the multi-probe peeping system observes a cavern excavation deformation and failure process of a cavern located within the test model dynamically in real time; and the hydraulic loading/unloading and steady pressure automatic control system comprises a visual human-machine interaction system, a PLC hydraulic system and a pressure execution system; the visual human-machine interaction system transmits and receives information to and from the PLC hydraulic system; and the PLC hydraulic system transmits and receives information to and from the pressure execution system.

15. An auto-controlled pressure true three-dimensional non-uniform loading/unloading and steady pressure model test system, comprising: a counterforce device; a pressure three-dimensional non-uniform loading/unloading device; a hydraulic loading/unloading and steady pressure automatic control system; an automatic model displacement test system; and a multi-probe peeping system, wherein the pressure three-dimensional non-uniform loading/unloading device is automatically controlled via an input instruction of the hydraulic loading/unloading and steady pressure automatic control system to carry out pressure three-dimensional gradient non-uniform loading/unloading and steady pressure control; the automatic model displacement test system automatically acquires displacement of any part inside a test model; and the multi-probe peeping system observes a cavern excavation deformation and failure process of a cavern located within the test model dynamically in real time; the automatic model displacement test system comprises a displacement transfer device, a displacement measuring device, a signal conversion device, a data processing device and a computer system; the displacement transfer device detects the displacement of the test model, the displacement measuring device transmits the displacement information to the signal conversion device, the signal conversion device transmits information to the data processing device, and the data processing device transmits information to the computer system; and when the test model produces a displacement, the displacement transfer device transfers the displacement of a model measuring point to the displacement measuring device via a flexible measuring rod, and the displacement measuring device converts the displacement of the test model measuring point into a moire fringe displacement via a grating ruler sensor; the signal conversion device converts the moire fringe displacement into an electric pulse signal via a photoelectric conversion element and transmits the electric pulse signal to the data processing device; the data processing device receives the electric pulse signal and converts the electric pulse signal into a digital signal, then model displacements are calculated, and stored and displayed on the computer system in real time, meanwhile, model displacement time-history curves are automatically generated for a tester to dynamically observe and monitor the displacement of the test model, so that digital and visual automatic measurement of the displacement of the test model is realized.

16. An auto-controlled pressure true three-dimensional non-uniform loading/unloading and steady pressure model test system, comprising: a counterforce device; a pressure three-dimensional non-uniform loading/unloading device; a hydraulic loading/unloading and steady pressure automatic control system; an automatic model displacement test system; and a multi-probe peeping system, wherein the pressure three-dimensional non-uniform loading/unloading device is automatically controlled via an input instruction of the hydraulic loading/unloading and steady pressure automatic control system to carry out pressure three-dimensional gradient non-uniform loading/unloading and steady pressure control; the automatic model displacement test system automatically acquires displacement of any part inside a test model; and the multi-probe peeping system observes a cavern excavation deformation and failure process of a cavern located within the test model dynamically in real time; and wherein the multi-probe peeping system comprises a plurality of probes, a camera control panel, a data storage box and a liquid crystal display; the plurality of probes are arranged at any inner or outer part of the cavern; and an acquired video is displayed on the liquid crystal display in real time and automatically stored in a data storage.

* * * * *